United States Patent
Witt et al.

(10) Patent No.: US 6,357,305 B1
(45) Date of Patent: Mar. 19, 2002

(54) METHOD AND DEVICE FOR SAMPLING DISPERSED STREAMS OF MATERIAL

(75) Inventors: Wolfgang Witt; Stephan Röthele, both of Clausthal-Zellerfeld (DE)

(73) Assignee: Sympatec GmbH, Clausthal-Zellerfeld (DE)

( * ) Notice: Subject to any disclaimer, the term of this patent is extended or adjusted under 35 U.S.C. 154(b) by 0 days.

(21) Appl. No.: 09/230,154

(22) PCT Filed: May 20, 1998

(86) PCT No.: PCT/EP98/02972

§ 371 Date: Aug. 9, 1999

§ 102(e) Date: Aug. 9, 1999

(87) PCT Pub. No.: WO98/53295

PCT Pub. Date: Nov. 26, 1998

(30) Foreign Application Priority Data

May 20, 1997 (DE) .......................................... 197 21 104

(51) Int. Cl.[7] .......................... G01N 1/20; G01N 15/02
(52) U.S. Cl. ................ 73/863.53; 73/863.61; 73/865.5
(58) Field of Search .................. 73/863.61, 863.52, 73/863.53, 863.56, 863.55, 863.57, 863.54, 863.44, 863.45, 865.5

(56) References Cited

U.S. PATENT DOCUMENTS

| | | |
|---|---|---|
| 3,783,695 A | 1/1974 | Grothe et al. |
| 3,784,902 A | 1/1974 | Huber |
| 3,885,437 A | 5/1975 | Reagan |
| 3,994,170 A | 11/1976 | Czarnecki |
| 4,061,036 A | * 12/1977 | Legille .................... 73/863.11 |
| 4,630,464 A | * 12/1986 | Meal et al. ................ 73/23.33 |
| 4,682,506 A | 7/1987 | Wienck et al. ........... 73/863.54 |
| 4,946,650 A | * 8/1990 | Röthe ................. 73/863.58 X |
| 4,950,073 A | 8/1990 | Sommer ..................... 356/37 |
| 5,052,425 A | * 10/1991 | Hohenberg et al. ...... 73/863.03 |
| 5,369,981 A | * 12/1994 | Metz et al. ............. 73/863.23 |

FOREIGN PATENT DOCUMENTS

| | | |
|---|---|---|
| DD | 121551 | 8/1976 |
| DE | 2631316 | 2/1977 |
| DE | 3210465 | 9/1983 |
| DE | 8513874 | 6/1985 |
| DE | 3422062 | 12/1985 |
| DE | 3543758 | 9/1986 |
| DE | 4115212 | 11/1992 |
| EP | 0388392 | 9/1990 |

OTHER PUBLICATIONS

Patent Abstracts of Japan P–1706, Mar. 9, 1994, vol. 18, No. 142 (S–322719).

* cited by examiner

*Primary Examiner*—Thomas P. Noland
(74) *Attorney, Agent, or Firm*—Dilworth & Barrese LLP

(57) ABSTRACT

The invention concerns a process for sampling disperse material flows in which an analysis substream is extracted from a process mainstream for subsequent analysis. According to the invention, the analysis substream is removed from the process mainstream via an extraction area. The extraction area is smaller than the process substream cross section and defined independently of this. The extraction area travels along an orbital curve across the process mainstream cross section during the removal of the analysis substream. The invention also relates to an apparatus for performing the process according to the invention.

37 Claims, 8 Drawing Sheets

SAMPLING TUBE

ROPRON

METHOD AND DEVICE FOR SAMPLING DISPERSED STREAMS OF MATERIAL

BACKGROUND OF THE INVENTION

The invention concerns a process for sampling disperse material flows in which, within a process mainstream, an analysis substream is taken from said process mainstream for subsequent analysis, and an apparatus for the performance of this process.

The size distribution of the particles or droplets, hereinafter referred to generally as particles, is of considerable importance for the production of disperse solids and emulsions as it essentially determines the reactivity, transport properties and stability of the material system.

Consequently, knowledge of the particle size distribution (PSD) enables the production process to be optimised and production to be geared to the required quality. To this end, an apparatus for determining the particle size distribution is necessary which can be integrated with ease at various points in the process without causing any noticeable disruption to the process sequence.

Devices for determining particle size distributions have long been well known and employ various measuring principles. In many applications, there is an increasing trend towards devices based on laser diffraction (LD) as this combines high measuring accuracy with good stability of the results, short measuring times, a wide measuring range, a low measuring range bottom limit and easy handling.

These devices utilise the fact that a particle irradiated by a monochromatic, coherent light deflects portions of this light with different degrees of intensity depending on its size, with small particles deflecting the light more intensively than large particles. This deflection of light is known as diffraction.

In a normal arrangement according to FIG. 1, a laser 1 followed by a divergent lens system 2 generates a dilated, parallel measuring light beam which illuminates particles 8 introduced into a measuring cell 7. The diffracted light is directed by a convergent lens 14, the Fourier optical system, onto a photodetector 16 with a multiplicity of elements which, together with a downstream electronics unit, enables the intensity distribution to be precisely mapped. The particle size distribution can then be calculated from this intensity distribution by means of an evaluation unit 20 using known algorithms.

Such an apparatus is equally suitable for determining the particle size distribution of disperse solids, suspensions and emulsions. Known calculation methods based on the Fraunhofer diffraction, yield a particle size distribution irrespective of the optical properties of the particles and those of the surrounding medium.

The suitability of these devices is, however, limited to the range of low particle concentration as operations are preferably performed by transmitted light and the measuring zone must allow the diffracted light to pass through. Moreover, the particle concentration must be kept sufficiently low so that the diffracted light is not diffracted again at downstream particles. This latter phenomenon, known as multiple scattering, can be taken into account when calculating the particle size distribution. The known algorithms for this purpose are limited to special particle forms and require precise knowledge of the optical parameters of the material system, a knowledge that is usually absent in relation to most particles.

The high mass flow rates which are usually encountered in production processes, often amounting to several tons per hour, therefore mean that it is necessary as a rule initially to remove from the process a sample or specimen and to reduce the particle concentration of this sample by addition of the medium surrounding the particles, i.e. by dilution, so that the maximum permissible particle concentration in the measuring zone is not exceeded. This process is only permissible for those material systems in which dilution does not alter the particle size distribution.

The sample in such cases has to be taken in a manner which ensures that the particle size distribution of said sample corresponds to the particle size distribution of the process in the time window under consideration, i.e. such that it is representative. This in turn requires that all areas of the transport cross section are equitably sampled and that the removal of the sample does not change the particle size distribution at the sampling location. If the process particles are incorporated in a flowing medium, then it is well known that the sample has to be removed isokinetically, i.e. that the particles are not allowed to undergo any velocity change as otherwise the particle size distribution of the sample would be noticeably altered as a result.

It is also well known in relation to laser diffraction that agglomerated particles are determined on the basis of their agglomerate diameter. In normal applications, it is the particle size distribution of the primary particles which is of primary interest. The agglomerated particles first have to be separated before they pass through the measuring zone. Various devices are known as being capable of performing this task, termed dispersion, which separate the dry particles in flows of high turbulence by causing the particles to impact against one another or to impact against the walls, or which use specifically introduced obstacles or apply centrifugal forces so that the particles become separated as a result of velocity gradients. Devices are known for suspensions in which a liquid, in some cases assisted by special chemical substances and the application of ultrasound, is used to separate the particles.

In order to eliminate from the calculated particle size distribution fluctuations in the optical properties of the components, e.g. the laser, and fluctuations in the efficiency of the Fourier optical system due to the presence of particles, from time to time a reference measurement is necessary in which the intensity distribution of the medium surrounding the particles is measured in the absence of particles.

Various devices have been proposed for determining particle size distributions within the process, but these only meet the indicated requirements in part, and usually only with considerable restrictions.

In the simplest known type of device, the laser diffraction system, is directly flanged onto the process piping, i.e. the entire process mass flow has to pass through the measuring zone. The high optical concentrations which occur in this case are adjusted on the basis of a material-dependent correction of the multiple scattering pattern. A reference measurement is only possible prior to commencement of a production phase (batch). The light source and detector are kept extensively clean by gas-purged tubes or by an enveloping flow passing along windows. Any contamination of the lens system which still occurs therefore falsifies the results in a protracted manner. Dispersion of the particles does not occur. Such a device is therefore only suitable for very small pipe diameters with production mass flow rates in the range of a few kg/h and where production times (batch times) are short. The analysed sample is rendered non-representative in its definition by the geometry of the measuring zone and the laser beam profile.

In another device, the light source and detector unit are integrated in a rod with an aperture transverse to the rod longitudinal direction, which is immersed through a flange into the process mass flow. The limitations of the above-mentioned type are extended by this non-representative sampling method, with particular problems being encountered in the case of this device with regard to keeping the windows clean.

In a further development, the first-mentioned device type is implemented with static, non-representative sampling in the bypass to a pipe of larger cross section. Sampling is performed at a fixed, definable position in the process pipe. Sample transfer is performed by a jet pump which further dilutes the analysis substream and is adjusted so that the sampling operation is performed as isokinetically as possible. The sampling tube is permanently open and exposed to the abrasive process mass flow. There is no provision for cleaning the sampling aperture. The analysis substream continuously passes through the measuring zone. It is accelerated by the jet pump and diverted several times until it is returned to the process. In order to reduce overall height, 90° elbows are used. This arrangement is unfavorable in relation to wear. The wear rate is proportional to the process mass flow and process time, and independent of the number of required measurements. The reference measurement can only be performed at the commencement of a batch.

In the case of another device type, the velocity of the process mass flow is first measured by differential pressure sensors through the incorporation of special flow geometries, and these values are used to adapt the pressure conditions in the analysis substream in order to ensure the isokinetics of the sampling operation. Particle size distribution analysis is performed by a laser diffraction system mounted at the outlet of the pipe, whereby, in one system configuration, the particles are initially separated at a filter and, on attainment of a certain sample quantity, this is measured with a laboratory laser diffraction system. Here, too, the sampling location is static, i.e. not representative of the entire cross section. The actual particle size distribution analysis takes place outside the piping system.

Such a sampling stage was also proposed for the case of through-flow piping with isokinetic sampling. Here again large analysis substreams occur which render sophisticated downstream stages necessary. Here, too, the actual particle size distribution analysis is performed outside the piping.

In order to improve the sampling situation, it was proposed in patent specification DE 35 43 758 C1 that a sampling segment rotate in the process pipe cross section. Where negligible flow occurs, the removal of a representative sample via the drop chute can be ensured. As a rule, the low division ratio renders repeated application of the principle necessary, a fact which, like the necessity of seals between the moving parts in the particle-laden environment, is disadvantageous. The actual particle size distribution analysis occurs outside the piping. To this end, the analysis substream is initially collected in an intermediate accumulator, then transported to the measuring system, whereby the measuring area can be adapted and blockage of the downstream stages avoided by sieving. There then follows a metering operation in a dry disperser, the measuring operation in a laser diffraction sensor, extraction of the aerosol and, where appropriate, return to the process via a cyclone and rotary-vane feeder. This solution has proven extremely effective, but at the same time is both bulky and expensive.

In the field of suspensions, all the solutions introduced to date have foregone the notion of representative sampling. In the devices usually employed for such applications, sampling is performed by a static tube extending into the process piping, or by a pneumatically extractable sampling finger (probe). The sample is conveyed by means of a diluting liquid. The dispersion stage is completely omitted or is performed in an agitated container by means of ultrasound. The diluted suspension is ultimately transferred by cuvette to the measuring zone of a laser diffraction system, and is then disposed of externally or returned to the process. For the reference measurement, the system is switched over to pure liquid by means of controlled valves.

Finally, devices have also been introduced in which other available sampling systems, such as impact samplers, Y valves, sampling screws etc. supply the samples and, once these have been appropriately prepared, analyse them with standard laser diffraction systems. Common to all these devices is that they are only suitable for certain special applications, require frequent maintenance and take up a considerable amount of space.

None of the prior art devices offers universal usability nor the combination of representative sampling for moving media with dispersion, concentration adaptation, a compact design and the possibility of performing a reference measurement with the process running.

The invention is thus based on the problem of providing a sampling method of maximum universal usability, and a compact apparatus for performing the sampling process. It should also offer the capability of representative, continuous sampling even at high production mass flows.

This problem is solved according to the invention by a method and process in which the analysis substream is removed from the process mainstream via an extraction area which is smaller than the cross sectional area of the process mainstream and is defined independently of this process mainstream cross section. During extraction of the analysis substream, the constant extraction area follows an orbital path which sweeps over the process mainstream cross section.

This sampling process according to the invention differs from the prior art methods and processes by virtue of its capability to enable a representative and continuous sampling operation which can also adapt the analysis flows to high production mass flows.

Taking as a basis for comparison the solution according to DE 35 43 758 C1, as it is shown in FIG. 2a, at a mass flow $\Theta$ (Mass flow M/Area) in a pipe, which cannot exceed certain values, a larger pipe diameter D is necessary for high mass flows (ROPRON is the trade name for the system shown);. In the solution according to DE 35 43 758 C1 with a rotating sampling segment, this necessarily leads to high analysis mass flows m as the minimum segment angle $\alpha$ is limited by the maximum particle size or by a multiple of this particle size. The governing equation reads as follows:

$$\dot{m} = \frac{\alpha}{2\pi}\dot{M} = \frac{\alpha}{2\pi}\Theta A_{Process} = \dot{m} \approx D^2$$
$$= \frac{\alpha}{2\pi}\Theta\frac{D^2}{4}\pi =$$
$$= \frac{\alpha}{8}\Theta D^2$$

i.e. the analysis mass flow $\dot{m}$ increases with the square of the process pipe diameter D.

FIG. 2b, on the other hand, shows that the likewise prior art solution with a sampling tube is considerably more favorable in this respect. The governing equation in this case is as follows:

$$\dot{m} = \frac{A_{Analysis}}{A_{Prozeß}}\dot{M} = \frac{\frac{d^2}{4}\pi}{\frac{D^2}{4}\pi}\dot{M} = \quad \dot{m} \approx d^2$$

$$= \frac{d^2}{D^2}\Theta A_{Prozeß} = \frac{d^2}{D^2}\Theta\frac{D^2}{4}\pi =$$

$$= \frac{\pi}{4}\Theta d^2$$

i.e. the analysis substream is now independent of the process pipe diameter and proportional to the square of the selectable diameter of the sampling tube d.

Isokinetic sampling with a static sampling tube is not representative. This problem is now solved by the invention in that the sampling tube travels over the cross section of the process pipe at constant velocity so that the entire cross sectional area or a representative proportion of that area is swept over n times during a measuring period. The orbit curve in this case must be selected so that all the individual zones are only passed once per sampling cycle.

Preferred embodiments of the process according to the invention are defined in claims 2–9.

Particularly advantageous devices for performing the process according to the invention are defined in claims 10–22.

Finally, devices according to the invention can be employed in a particularly advantageous manner for various measuring processes as claimed in claims 23–26.

Devices for determining particle sizes and/or particle size distributions are derived from disclosure herein.

BRIEF DESCRIPTION OF THE DRAWINGS

Further details and advantages of the invention are described more closely on the basis of the example embodiments shown in the drawings, wherein.

DESCRIPTION OF THE PREFERRED EMBODIMENTS

Figure 1:
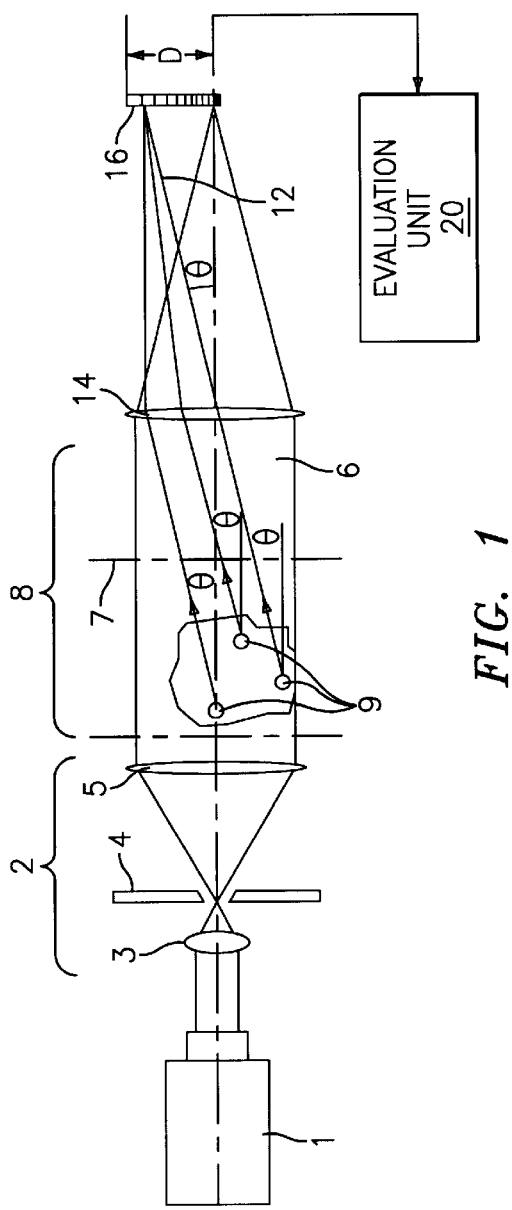
FIG. 1 shows a prior art laser diffraction system.
Figure 2B:
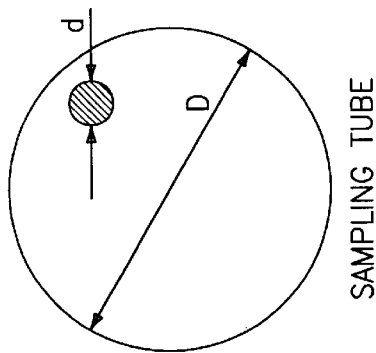
FIG. 2 shows various sampling geometries for representative sampling according to prior art technology using a segment (FIG. 2a) or a sampling tube (FIG. 2b)
Figure 2A:
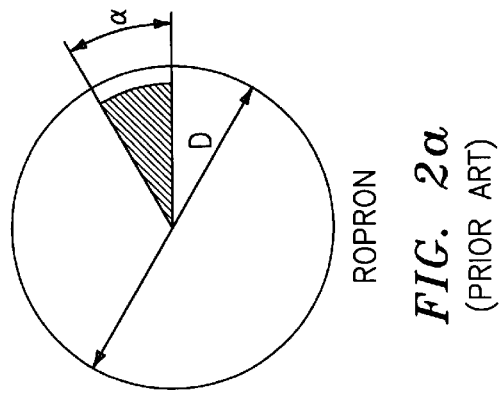
Figure 3:
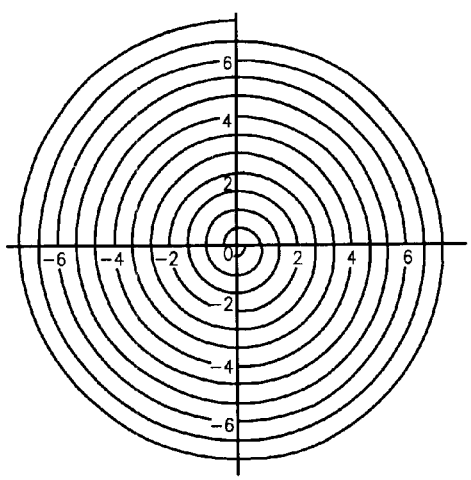
FIG. 3 shows the spiral orbit traced by a sampling tube according to the invention.
Figure 4:
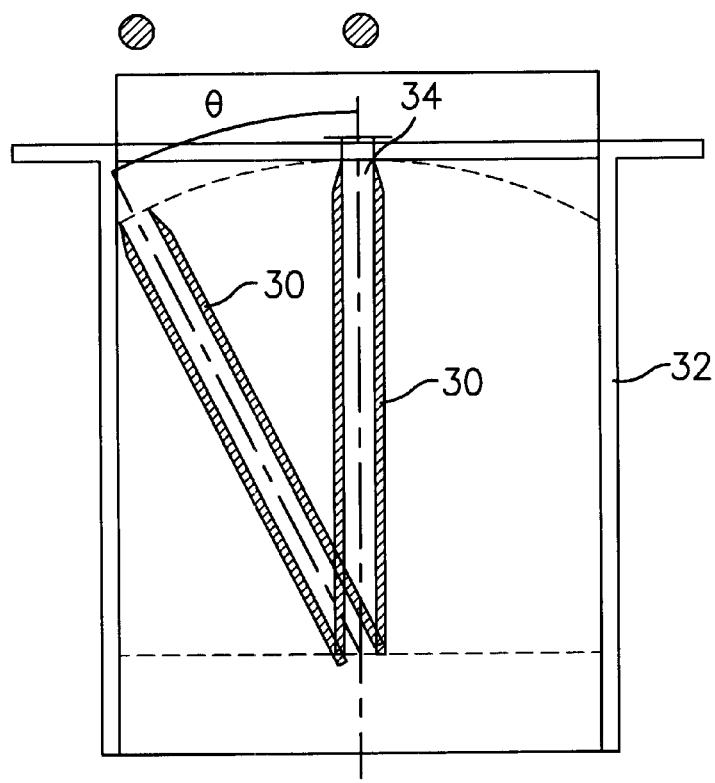
FIG. 4 shows a diagrammatic representation of an embodiment of the sampling tube according to the invention.

FIG. 4 shows a schematic of a sampling tube 30 which is mounted in the center of a process pipe 32 and is directed towards the product flow, not illustrated in any detail here, at a shallow angle Θ. The aperture 34 of the sampling tube 30 traces a spiral orbit such as that indicated in FIG. 3 and defined by the following equations:

$$r(\tau) = \frac{D}{2}\frac{\tau}{\frac{t_p}{2}} = D\frac{\tau}{t_p}$$

$$w_o = 2n\frac{2\pi}{t_p} = 4\pi\frac{n}{t_p}$$

τ(t) should be selected as a function of time t so that the orbiting speed v(t) is constant. Here, the following approximate equation applies $$w(t) = \frac{w_o}{r(\tau)}$$

where
D: process pipe diameter
n: number of 360° orbits required to the centre
$t_p$: total sampling time In order to avoid sampling errors, it is necessary to extract the analysis substream isokinetically. The particle velocity in pipes is generally a function of the radius r measured from the centre of the process pipe. In a preferred apparatus according to the invention, the negative pressure in the sampling tube is modified for this purpose using empirically determined values so that the sampling operation is performed isokinetically irrespective of r.

The sampling tube is exposed to the process mass flow and thus undergoes extreme wear. This particularly applies at high particle velocities, e.g. in pneumatic handling applications. In order to minimise wear, internals should not exhibit surfaces which are perpendicular to the direction of flow. It is also imperative that deflections of the analysis substream be limited to small angles so that there, too, wear is minimised. Finally, all components of the sampling tube should be manufactured from carbides, ceramics or other wear-resistant materials. The travel distances should also be kept as short as possible for reasons of cost. Transportation of the sample outside the process pipe leads to large tubing lengths and large overall heights if 90° elbows are to be avoided.

Aperture 34 of sampling tube 32 describes a spiral orbit at an orbiting speed v.

As the projected area of the inlet aperture changes with cos(Θ), this must be compensated for as a function of orbiting speed in order to attain a representative sampling operation, as follows:

$$v(\theta) = v_o \cos(\theta)$$

Figure 5:
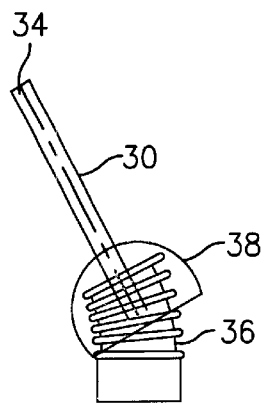
FIG. 5 shows an embodiment of the sampling tube according to the invention with bellows and shield.

This design does not require that the sampling tube rotates relative to the process pipe. Consequently, it can be connected by elastic walls free of seals. In a preferred embodiment, the connection is provided by a metal bellows 36 which is mechanically protected against the particles of the process mass flow by a shield 38 as shown in FIG. 5.

The reference measurement which has to be performed occasionally means that it is necessary for the medium surrounding the particles to be ducted particle-free through the measuring zone. In the case of the prior art devices, controlled valves and/or controlled metering units are employed for this purpose which enable the particle flow to be interrupted for the duration of the reference measurement. In the case of the proposed sampling system, it is sufficient for this purpose to retract the sampling aperture from the product feed and/or to seal the sampling aperture, or to connect it to the medium surrounding the particles. The sampling aperture must, furthermore, be cleaned from time to time to remove deposits and blockages resulting from the presence of coarse particles, fibres etc. Moreover, the sampling aperture should be prevented from being exposed to the process mass flow during non-measuring phases, in order to minimise overall wear.

Figure 6:
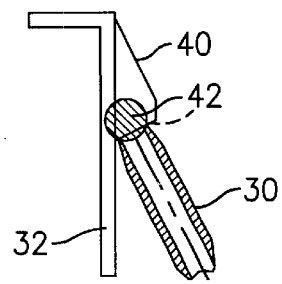
FIG. 6 shows an embodiment of the invention with a sampling tube at its parking position (with pressure ball seal)

In the embodiment illustrated in FIG. 6, for this purpose a protected parking position 40 is provided inside the process pipe 32 such that it exerts minimal resistance to the flowing particles, simultaneously effectively seals the sampling tube 30 (e.g. by means of pressure ball seal 42 as per FIG. 6) or it connects the sampling tube to a port for the particle-free medium. An integrated wiper performs the cleaning operation as the tube aperture enters the parking position.

In an embodiment, several parking positions may be distributed around the inside of the process pipe so that the sampling aperture can be moved from one parking position to another. By using e.g. linear scans across the tube center, the residence time of the sampling aperture in the process mass flow, and thus the degree of wear, can be further reduced subject to limitations in representativity.

Figure 7:
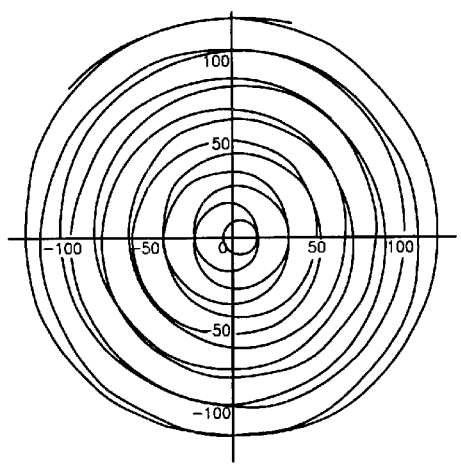
FIG. 7 shows a spiral orbit of the sampling aperture in the sampling tube which begins and ends at the parking position.

In a preferred embodiment of the invention, the orbital curve of the sampling aperture is described by a spiral which starts at the parking position at the process pipe wall, follows a spiral path towards the center and finally, in a continuation of the spiral orbit, ends again at the same parking position (FIG. 7). Such an orbit curve can be generated in various ways.

Figure 8A:
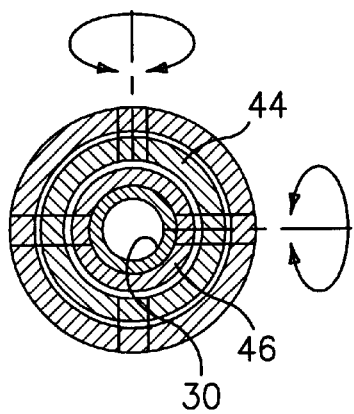
FIG. 8 shows a drive arrangement for a sampling tube according to an embodiment of the invention, with universal joint mounting and push rods.
Figure 8B:
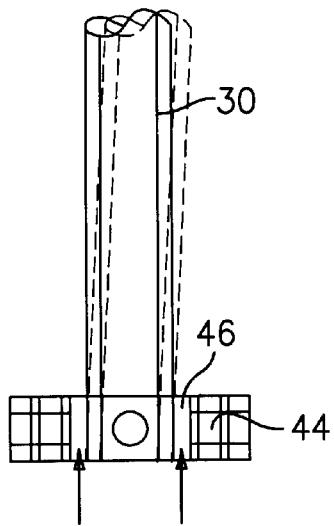

In the apparatus according to FIGS. 8(*a*)(*b*), the sampling tube 30 is mounted in a universal joint at the center of pipe for this purpose. By means of controlled manipulation of the two cardan rings 44, 46 illustrated in FIGS. 8(*a*) and (*b*), the tube is tilted around the two mutually perpendicular angles θ and φ in respect of the tube axis. By controlling the temporal sequence of this tilting action, the sampling aperture can trace any predetermined orbital curve. The manipulation of the cardan rings 44, 46 may be performed e.g. by push rods or hydraulic rams. The drive power can be provided from outside the pipe, e.g. by stepping motors. When employing push rods, a simple lever mechanism can be incorporated to facilitate 90° force transmission.

Figure 9:
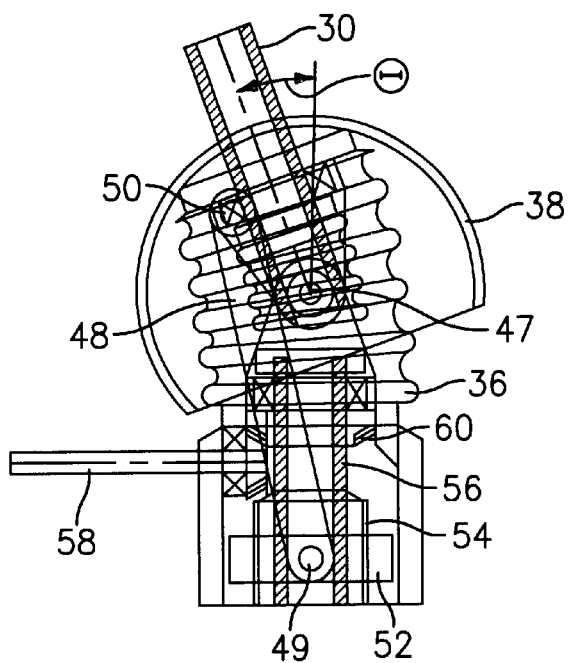
FIG. 9 shows a preferred embodiment, according to the invention, of the drive arrangement for the sampling tube.

In the embodiment illustrated in FIG. 9, the spiral orbit is derived from a simple rotary motion. To this end, the sampling tube 30 is mounted at one end on a shaft 47 running perpendicular to the tube axis. The sampling tube 30 is tilted by a push rod 48 which is pivot-connected by a bearing 50 to a lever attached to said sampling tube 30. The axis of the pivot bearing 50 runs parallel to the axis of shaft 47. The other end of the push rod 48 is pivot-mounted to a threaded nut 52 via a bearing 49. The threaded nut 52 runs on a thread 54 which is permanently connected to a delivery tube 56. The sampling tube 30 together with the push rod 48 and the threaded nut 52 can be rotated in relation to the delivery tube 56, and the thread 54 rigidly connected to it, by means of a rotary rod mechanism 58 and a gear rim 60. During this rotation, the threaded nut 52 moves around the fixed thread 54 so changing, via the push rod 48, the angle Θ of the sampling tube 30 relative to the pipe axis. The sampling aperture rotates around the process pipe axis and in so doing describes a spiral orbit.

The deflection r of the sampling aperture from the process pipe centerline as a function of deflection x of the bearing from the position ($x_o$) at which the sampling tube is located at the centre of the process pipe, is described by the following equation:

$$r(x) = -\frac{1}{2}\frac{(-\sqrt{l^2 - H^2x} + x^2)L}{(-\sqrt{l^2 - H^2} + x)H}$$

Figure 10:
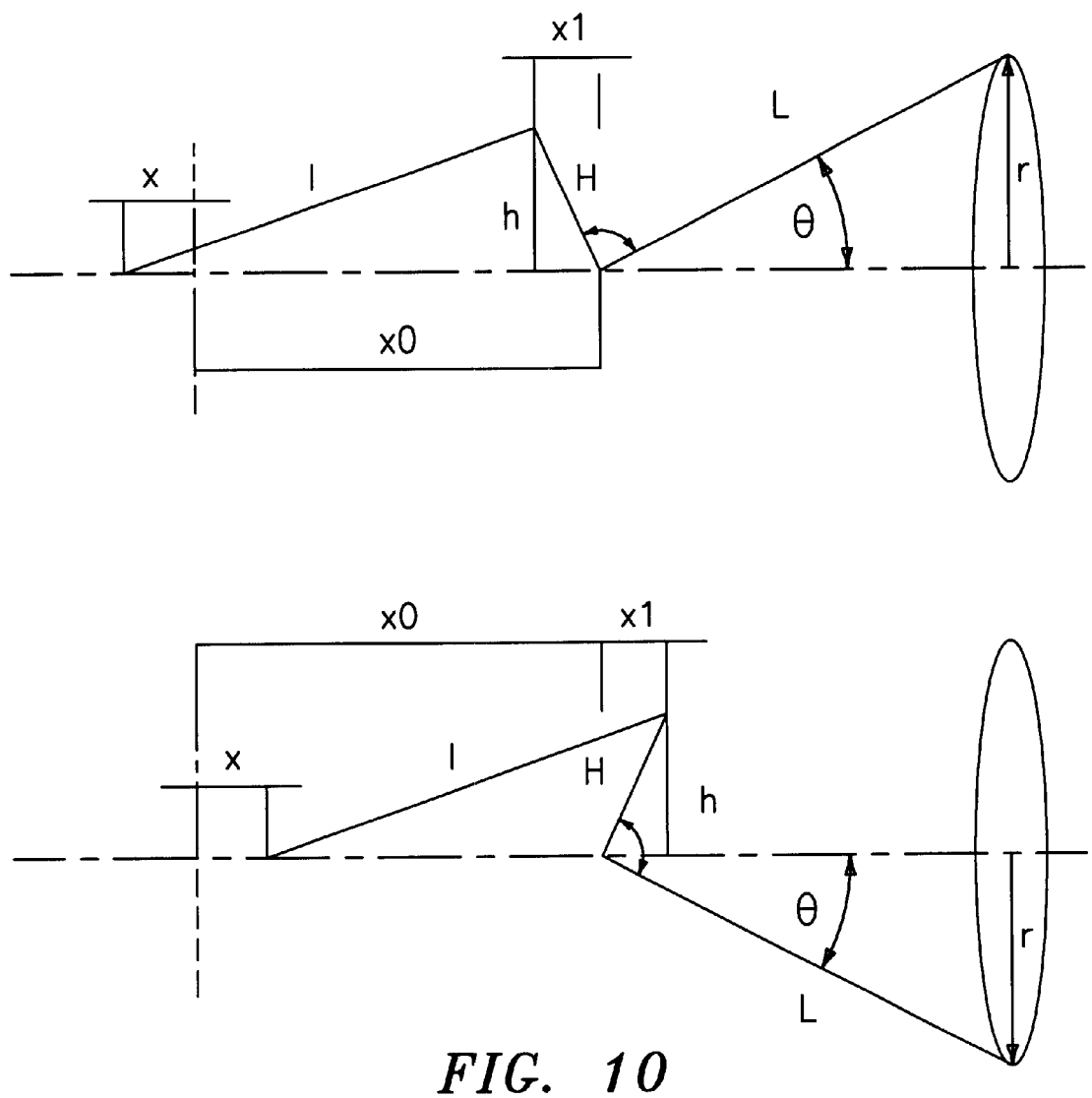
FIG. 10 shows a diagram for calculating the movement equation of the aperture of the sampling tube.

L here is the length of the sampling tube. Where L=168.5 mm, H=10 mm and I=79.2 mm, the approximately linear relationship is yielded as illustrated in FIG. 10. The orbital curve in FIG. 6 has been calculated with these parameters for a thread pitch of 1 mm/turn. It starts at the parking position at the edge and passes via the center back to the edge without the direction of rotation of the motor having to be changed. To repeat the operation, it is sufficient to change the direction of rotation of the motor at the parking position, i.e. at standstill. This can be implemented, for example, by means of a simple sensor which detects the arrival of the sampling tube at the parking position, whereupon a control system stops the drive unit and reverses the direction of rotation of the motor for a further scan. FIG. 10 shows a diagram for calculating the above-mentioned movement equation.

The suggested sampling process according to the invention thus exhibits considerable advantages over prior art devices and processes: a) Sampling is performed only during the measuring period, otherwise the sampling aperture is in the parking position where it is protected from the process mass flow. The wear of the sampling apparatus, the dispersion section and the measuring system is thus reduced by several orders of magnitude. b) While the process is running, a reference measurement can be taken at any time at the parking position. No further measures are necessary for this purpose. c) The drive arrangement requires no seals to isolate it from the process mass flow and is only required to move small masses. Consequently, only a low level of drive power is necessary. d) The sampling operation is continuous and representative in terms of time and location. Thanks to the large diameter ratio D/d, the main process flow is only affected to a very small extent by the sampling operation. The analysis substream remains independent of the process pipe diameter and can be easily adapted to the requirements of the measuring system by altering the size of the aperture of the sampling tube. The integrated cleaning mechanism renders an upstream protective sieving arrangement dispensable.

The reduction in the free cross section of the process pipe resulting from the requisite internals can be compensated for by increasing the pipe diameter below the plane of the sampling aperture. Any influence on the sampling operation can also be extensively precluded in such cases.

Various methods are known for dispersing disperse solids in gas or liquids. For dispersion in gases, the methods used are particle-wall impact, particle-particle impact and/or centrifugal forces such as those which occur, for example, as a result of velocity gradients in a shear flow. The energy provider can take the form of e.g. a jet pump. Ultrasound is frequently employed for dispersing suspensions. In the preferred embodiment according to FIG. 11, a jet pump 62 is arranged coaxially within the process pipe 63 at the outlet of the sampler. The negative pressure necessary for particle transport is generated in the sampling tube by the injection of propellant gas or suspension liquid. The propellant flow pressure generated by the jet pump 62 is selected such that, using empirically determined parameters, it produces an isokinetic condition at the sampling tube 30. The injected medium dilutes the analysis mass flow. The energy supplied is used for dispersion.

Figure 12:
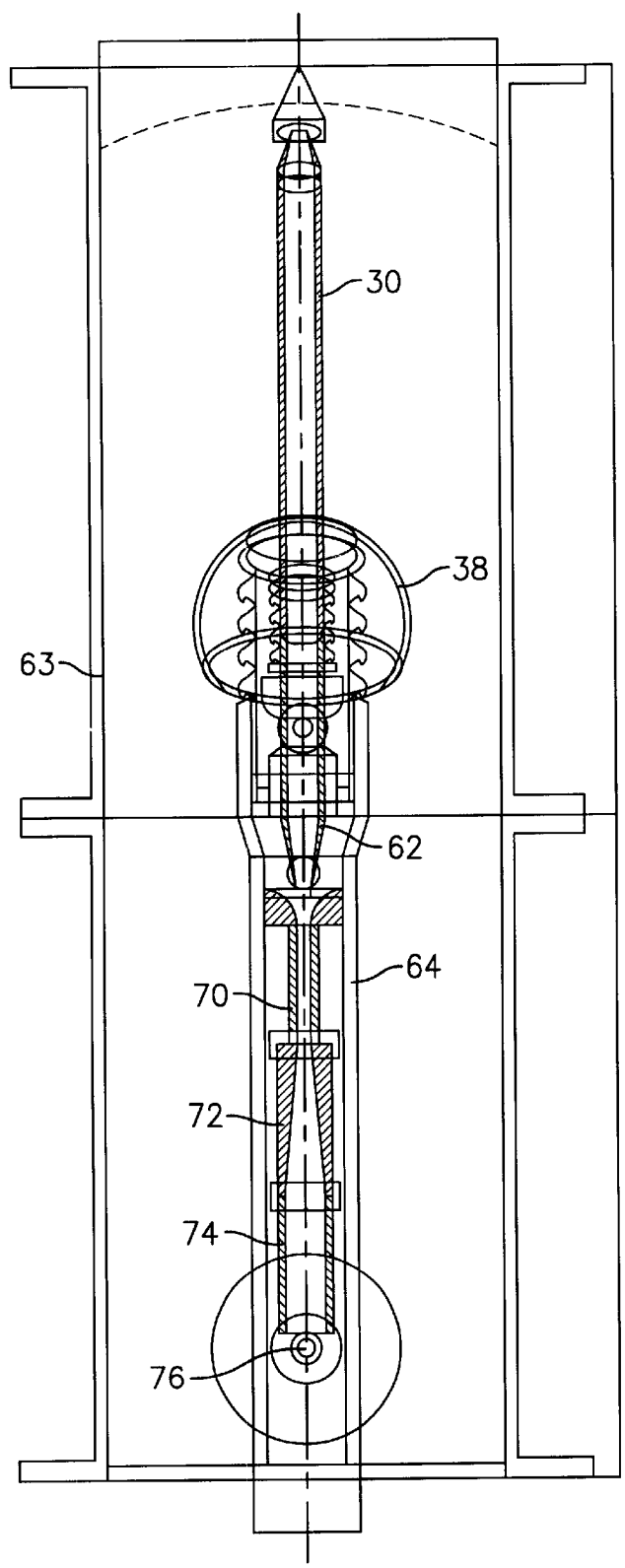
FIG. 12 shows a side view of the apparatus of FIG. 11 in a slightly modified form and rotated 90°.
Figure 13:
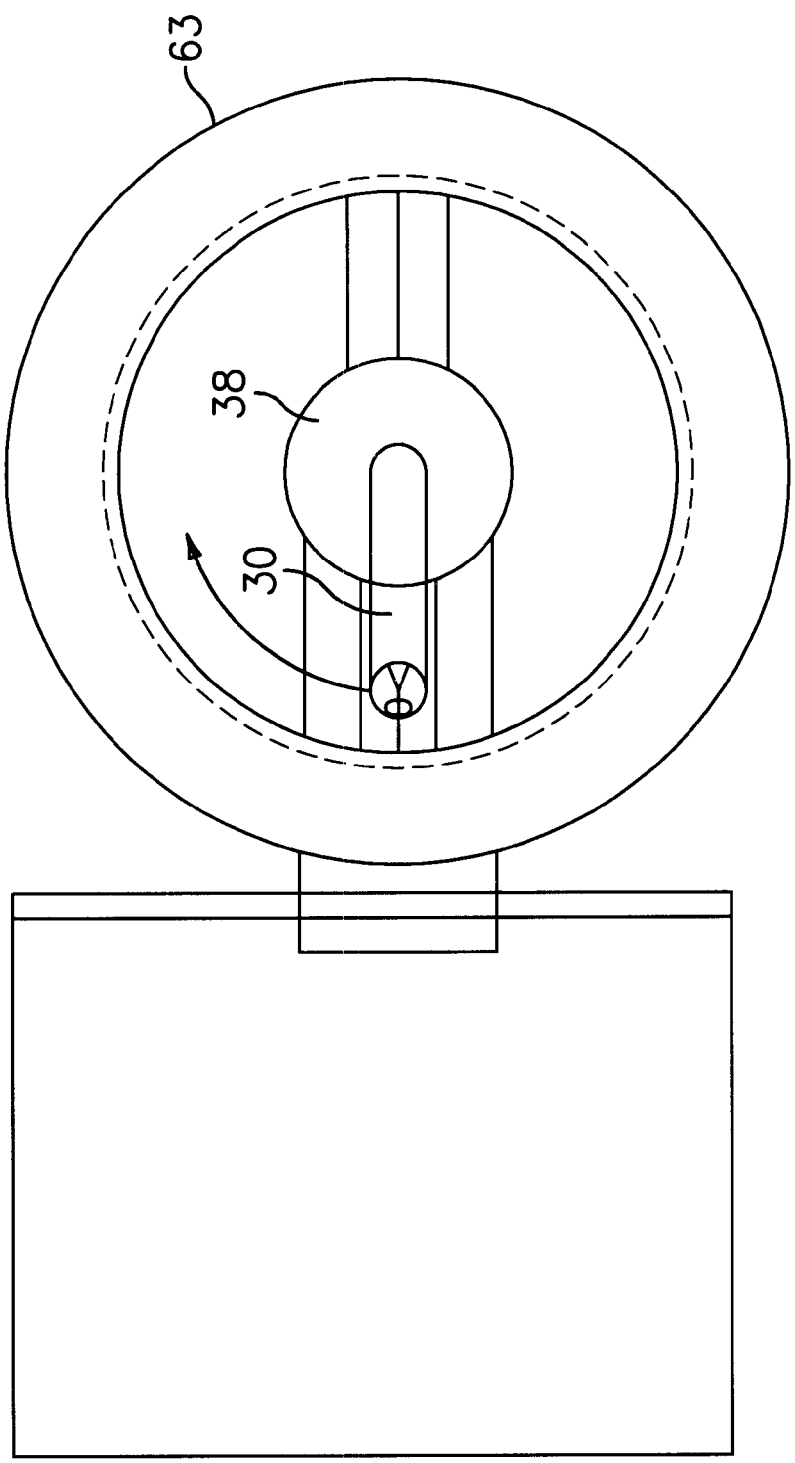
FIG. 13 shows a plan view of the apparatus according to FIG. 11 viewed from the top onto the sampling tube.

For solid aerosols, there is connected to the apparatus, in a preferred embodiment of the invention according to FIG. 12, a jet ducting tube 70 with a round cross section. The cross section is dimensioned so that it is sufficiently narrow to produce as many particle-particle and particle-wall impacts as possible. Connected to it is a downstream transition tube 72 in which the cross section continuously increases while at the same time changing from round to square. Finally, this is followed by a downstream jet ducting tube 74 with a square cross section which extends to just in front of the measuring zone 76. The square cross section prevents the gas jet, which cools as it expands, from producing a lens effect in the measuring zone.

In a preferred embodiment of the invention, blockages in the sampling tube can furthermore be removed by causing the outlet from the jet pump to be briefly closed. This can be implemented, for example, by closing the jet ducting tube. Here, the jet ducting tube is moved to a point where its wall almost completely closes off the outlet opening. The propellant then escapes via the sampling tube, so removing any deposits and blockages by its scavenging action.

In a preferred embodiment of the invention for suspensions, a downstream cross sectional expansion stage with static mixer is provided into which the ultrasound sonotrode protrudes. The sonotrode is connected by a jacket tube to the ultrasonic generator, which is arranged outside the process pipe. A layer of air between the sonotrode and the jacket tube prevents direct sound transmission to the process suspension. The cross sectional expansion reduces particle velocity and increases the duration of exposure to the ultrasound. The static mixer homogenizes the diluted suspension.

In the case of optical processes for determining particle size distributions, such as laser diffraction or image processing, the optical concentration $C_{opt}$ must lie within certain limit values. $C_{opt}$ for monodisperse particles with diameter x is calculated for the preferred embodiment of the invention as follows:

$$C_{opt} = \frac{3}{2}\left(\frac{d}{D}\right)^2 \frac{\kappa \dot{m}}{b v \rho x}$$

where d is the diameter of the sampling aperture, D is the diameter of the process pipe, κ is the extinction coefficient, $\dot{m}$ is the process mass flow, b is the width of the jet ducting tube, ρ is the specific density and v is the velocity of the particles in the measuring zone. For non-monodisperse particles, the relationship can also be similarly described.

Figure 11:
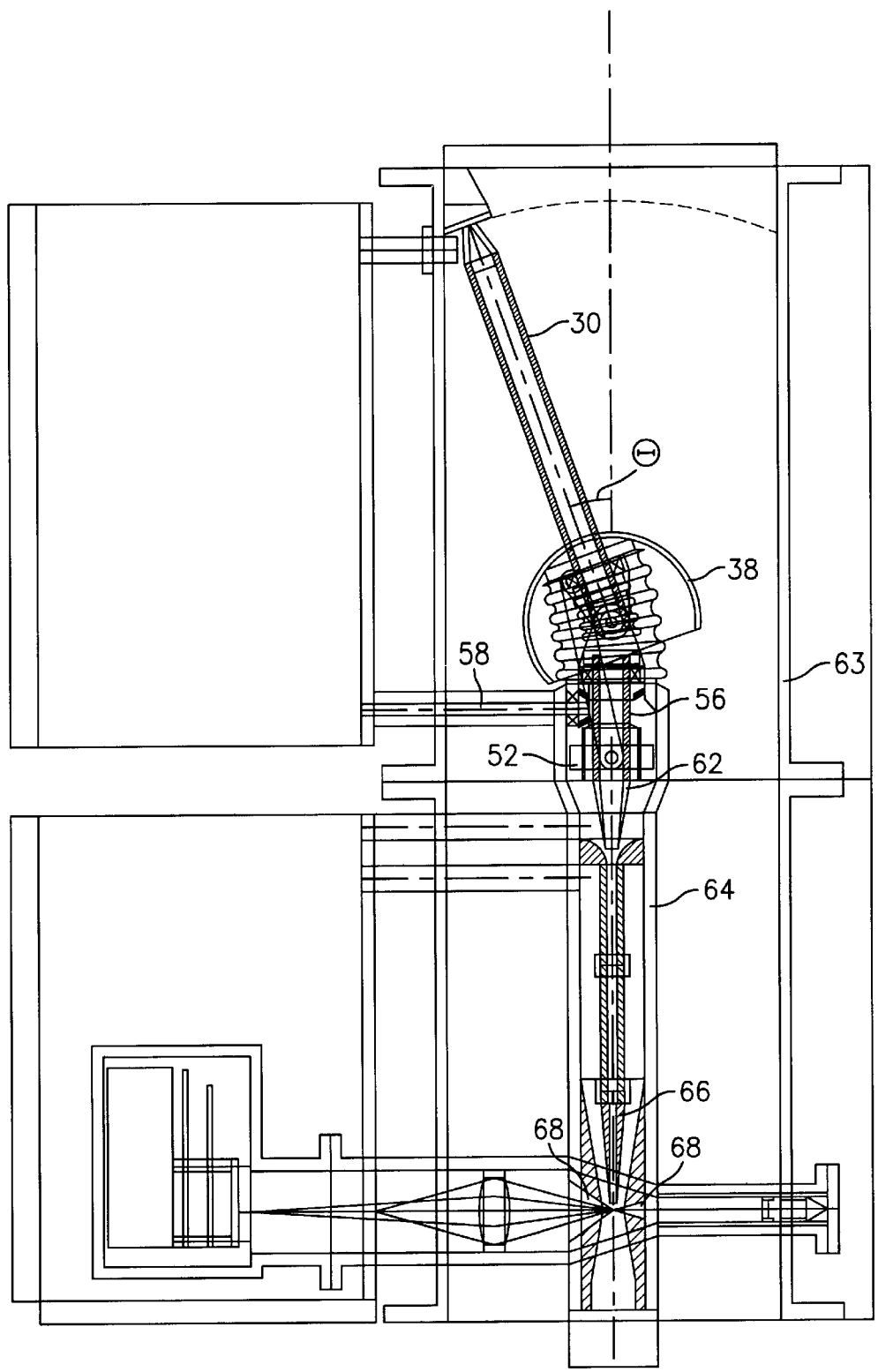
FIG. 11 shows a side view of a complete measuring device for performing sampling, dispersion, dilution, particle size distribution determination by laser diffraction, and sample return.

In the embodiment according to FIG. 11, the velocity of the particles is increased in a second jet pump 66 such that the particles are preferably located at the center of the measuring zone and necessary windows 68 are not contaminated. The injected medium dilutes the analysis substream and alters the particle velocity v. The optical concentration can thus be statically adapted via D, d and b, and dynamically adapted via V.

In the apparatus, the measurement of the particle size distribution following the dilution stage is performed using prior art processes, e.g. by means of laser diffraction or image processing. In this process, the components necessary are supplied via one or several jacket tubes from the outside through the process pipe to the dilution stage. The jacket tubes are tightly connected to the jacket tube of the dilution stage. The optical components of the measuring system are protected by optical windows from the particles of the analysis mass flow.

The analysis substream is returned in the apparatus described here via jacket tube 64 directly downstream of the measuring zones in the direction of the pipe axis. The outlet is open. The coaxial design and alignment along the process pipe axis is particularly beneficial compared with prior art processes involving a return via lateral connections; the fast-moving particles only impact against the process pipe wall at very shallow angles and the wear of this wall is thus considerably reduced. As the particles remain within the process pipe, no additional measures are necessary while the process pipe is under pressure. The need for a return feed mechanism (pump) is eliminated.

In a further embodiment of the invention, a valve is located at the outlet, e.g. a pinch valve which closes the outlet when required and, for example, prevents steam employed for cleaning the process pipe, liquid or solids from reaching the measuring zone.

Aside from the optical processes such as laser diffraction or image processing, ultrasound extinction (UE) is becoming increasingly important as a means for determining particle size distribution.

Ultrasound extinction determines the sound wave attenuation for various frequencies. In a manner similar to that of laser diffraction, here, too, the particle spectrum is measured in transmission, i.e. the sound wave emitted by a sound transmitter penetrates the measuring zone and, in a weakened condition, reaches a sound receiver. The measured attenuation can be used to determine the size distribution of the particles using known algorithms.

These algorithms place requirements on the frequency range in relation to the particle size to be determined. In practical applications, very high frequencies in the range 100 kHz to several 100 MHz are involved which can only be coupled in liquids in order to achieve sufficient efficiency. Ultrasound extinction is thus limited to applications involving the determination of the size distribution of particles in liquids.

In contrast to laser diffraction, optical transparency plays no role at all in such applications, while the roles played by multiple scattering and dispersion are very subordinate. Measurements can therefore be carried out on very high concentrations without dilution and without dispersion. This is advantageous in the case of material systems in which dilution would change the size distribution of the particles (e.g. in crystalization).

The attenuation of the sound wave by the liquid limits the maximum possible distance between the sound transmitter and receiver to just a few millimeters particularly in the case of high frequencies, i.e. fine particles. This minimal distance consequently limits the possible volume flow which can pass through the measuring zone.

Again, a reference measurement performed from time to time on the particle-free liquid improves the stability of the results.

The available calculation methods also require knowledge of the acoustic parameters of the material system, and particularly the extinction function. This can be determined for a group of like material systems, e.g. by comparing with other measuring processes.

Ultrasound extinction is thus particularly suitable for processes in which dilution would alter the size distribution and in which a product change is rare.

In a further preferred apparatus according to the invention, the described sampling arrangement is combined with an ultrasound extinction system. In order to retain the advantage of ultrasound extinction whereby particle size distributions can be measured without dilution and without dispersion, the measuring system is arranged immediately downstream of the sampling stage. Sample transport is performed by a downstream, variable-speed pump. This may be a jet pump, for example, in cases where the injection of liquid into the process is harmless. For simple applications, the pressure differential can also be utilised which arises from the restriction of the process pipe upstream of the outlet to the return line.

What is claimed is:

1. Process for sampling disperse material flows in which an analysis substream is removed from a process mainstream for subsequent analysis, wherein
    the analysis substream is taken from the process mainstream via an extraction area which is smaller than the process mainstream cross-section and is defined independently of the same,
    the extraction area follows an orbital curve across the process mainstream during extraction of the analysis substream, and
    the constant extraction area is guided along a spiral orbit across the process mainstream cross section.

2. Process according to claim 1, wherein the extraction area is the circular cross section of the aperture of a sampling tube.

3. Process according to claim 1, wherein the process mainstream passes through a pipe.

4. Process according to claim 1, wherein that the constant extraction area is moved along an orbital curve across the process mainstream cross section such that the locations scanned during a sampling cycle contribute equally to the analysis substream.

5. Process according to claim 1, wherein the inlet of the constant extraction area is sealed or isolated if the sampling operation is to be interrupted.

6. Process according to claim 1, wherein isolation of the constant extraction area is performed by moving the constant extraction area to a parking position which is designed to prevent the ingress of particles from the process mainstream into the sampling tube.

7. Process according to claim 1, wherein the extraction velocity of the analysis substream is adjustable.

8. Process according to claim 7, wherein the analysis substream is extracted at a velocity which is equal to the velocity in the environment surrounding the sampling aperture (isokinetic extraction).

9. Apparatus structured and arranged for performing a process according claim 1, wherein arranged within the process mainstream, is a traversible sampling tube aligned in the direction opposite to the direction of the disperse material flow.

10. Apparatus according to claim 9, wherein the sampling tube is connected to an extraction device such that the extraction velocity at the extraction area defined by the aperture of the sampling tube can be adjusted by said extraction device.

11. Apparatus according to claim 9, wherein the sampling tube is arranged at the centre of a pipe through which the process mainstream flows.

12. Apparatus according to claim 11, wherein the sampling tube can be continuously actuated through its orbit, which begins at the parking position and then ends at the same parking position, without a reversal to the direction of rotation of the motor, and that, only on a repeat operation starting at the parking position, is the direction of rotation of the motor to be reversed.

13. Apparatus according to claim 9, wherein the sampling tube is pivot mounted to allow rotation and tilting in relation to the process pipe axis, and that during the rotary motion it can be deflected by a positively connected push rod.

14. Apparatus according to claim 9, wherein a mechanism for slewing the sampling tube can be isolated from a pipe carrying the process main stream by means of moving walls, without sealing elements.

15. Apparatus according to claim 14, wherein the movable walls are bellows.

16. Apparatus according to claim 9, wherein, in order to avoid blockages, the aperture of the sampling tube (extraction area) is smaller than the inside diameter of the sampling tube.

17. Apparatus according to claim 9, wherein the aperture of the sampling tube (extraction area) can be adapted to the measuring system requirements by means of interchangeable caps which can be fitted to the sampling tube.

18. Apparatus for determining at least one of particle sizes and particle size distributions containing a device for sampling disperse material flows according to one of claim 9, wherein the sampling device, a sample transport system, a dispersing system, a measuring zone and a sample return stage are arranged within a pipe in the order recited.

19. Apparatus according to claim 18, wherein the measuring process is based on laser diffraction, ultrasound extinction or image analysis.

20. Apparatus according to claim 18, wherein a valve is arranged at the outlet of the apparatus.

21. Apparatus according to claim 20, wherein the valve is a pinch valve.

22. Apparatus for performing a process for sampling disperse material flows in which an analysis substream is removed from a process mainstream for subsequent analysis, wherein
    the analysis substream is taken from the process mainstream via an extraction area which is smaller than the process mainstream cross-section, is defined independently of the same,
    the extraction area follows an orbital curve across the process mainstream cross-section during extraction of the analysis substream,
    said apparatus arranged within the process mainstream being a traversible sampling tube aligned in the direction opposite to the direction of the disperse material flow,
    the sampling tube is pivot mounted to allow rotation and tilting in relation to the process pipe axis,
    during the rotary motion, the tube can be deflected by a positively connected push rod, and,
    the tilting motion imparted by the positively connected push rod can be generated, during the rotational movement of the sampling tube, via a threaded nut screwed onto a thread which is permanently fixed to the delivery tube.

23. Application of an apparatus for performing a process for sampling disperse material flows in which an analysis substream is removed from a process mainstream for subsequent analysis, wherein the analysis substream is taken from the process mainstream via an extraction area which is smaller than the process mainstream cross-section and is defined independently of the same, and the extraction area follows an orbital curve across the process mainstream cross-section during extraction of the analysis substream, said apparatus arranged within the process mainstream, being a traversible sampling tube aligned in the direction opposite to the direction of the disperse material flow, and in a process to determine at least one of particle sizes and particle size distribution in pipes using methods based on at least one of laser diffraction, image processing and ultrasound extinction, with the sampling device, a sample transport system, a measuring zone and a sample return system being arranged within the pipe parallel to the pipe axis, and with a partial flow (substream) being removed by the sampling device, which then passes through the apparatus shielded from the remaining process mass flow, and downstream of the sample return system being immediately reunited with the process mass flow.

24. Application according to claim 23, wherein a dispersing stage is additionally arranged within the pipe parallel to the pipe axis.

25. Application according to claim 23, wherein, in a process for determining at least one of particle sizes and particle size distributions in pipes using methods based on at least one of laser diffraction and image processing, the sampling device, sample transport system, the measuring zone and the sample return system are sequentially arranged within the pipe in the order cited.

26. Application according to claim 23, wherein, in a process for determining at least one of particle sizes and particle size distributions in pipes using methods based on ultrasound extinction, the sampling device, the measuring zone, sample transport system and the sample return system are sequentially arranged within the pipe in the order cited.

27. Apparatus for performing a process for sampling disperse material flows in which an analysis substream is removed from a process mainstream for subsequent analysis, wherein the analysis substream is taken from the process mainstream via an extraction area which is smaller than the process mainstream cross-section and is defined independently of the same, the extraction area follows an orbital curve across the process mainstream cross-section during extraction of the analysis substream, said apparatus arranged within the process mainstream being a traversible sampling tube aligned in the direction opposite to the direction of the disperse material flow, and several parking positions are provided on the pipe which are designed to prevent the ingress of particles from the process mainstream.

28. Apparatus according to claim 27, wherein a cleaning device is arranged in a parking position which cleans the sampling aperture as the sampling tube enters and leaves said parking position.

29. Apparatus for performing a process for sampling disperse material flows in which an analysis substream is removed from a process mainstream for subsequent analysis, wherein the analysis substream is taken from the process mainstream via an extraction area which is smaller than the process mainstream cross-section and is defined independently of the same, the extraction area follows an orbital curve across the process mainstream cross-section during extraction of the analysis substream, said apparatus arranged within the process mainstream being a traversible sampling tube aligned in the direction opposite to the direction of the disperse material flow, and the sampling tube is mounted in two cardan rings in the process pipe and can be deflected by swiveling the cardan rings under time control.

30. Apparatus according to claim 29, wherein the sampling tube in its parking position can be connected via a valve to a particle-free fluid.

31. Apparatus for determining at least one of particle sizes and particle size distributions containing a device for sampling disperse material flows for performing a process for sampling disperse material flows in which an analysis substream is removed from a process mainstream for subsequent analysis, wherein the analysis substream is taken from the process mainstream via an extraction area which is smaller than the process mainstream cross-section and is defined independently of the same, and the extraction area follows an orbital curve across the process mainstream cross-section during extraction of the analysis substream, said apparatus being arranged within the process mainstream and a traversible sampling tube aligned in the direction opposite to the direction of the disperse material flow, wherein the sampling device, a sample transport system, a dispersing system, a measuring zone and a sample return stage are arranged within a pipe in the order recited, and the sample transport is performed by a jet pump.

32. Apparatus for determining at least one of particle sizes and particle size distributions containing a device for sampling disperse material flows for performing a process for sampling disperse material flows in which an analysis substream is removed from a process mainstream for subsequent analysis, wherein the analysis substream is taken from the process mainstream via an extraction area which is smaller than the process mainstream cross-section and is defined independently of the same, and the extraction area follows an orbital curve across the process mainstream cross-section during extraction of the analysis substream, said apparatus being arranged within the process mainstream and a traversible sampling tube aligned in the direction opposite to the direction of the disperse material flow, wherein the sampling device, a sample transport system, a dispersing system, a measuring zone and a sample return stage are arranged within a pipe in the order recited, and the dispersing operation in liquid systems is performed by an ultrasound probe which is isolated from the process pipe by a layer of air.

33. Apparatus for determining at least one of particle sizes and particle size distributions containing a device for sampling disperse material flows for performing a process for sampling disperse material flows in which an analysis substream is removed from a process mainstream for subsequent analysis, wherein the analysis substream is taken from the process mainstream via an extraction area which is smaller than the process mainstream cross-section and is defined independently of the same, and the extraction area follows an orbital curve across the process mainstream cross-section during extraction of the analysis substream, said apparatus being arranged within the process mainstream and a traversible sampling tube aligned in the direction opposite to the direction of the disperse material flow, wherein the sampling device, a sample transport system, a dispersing system, a measuring zone and a sample return stage are arranged within a pipe in the order recited, and for solid aerosols, a jet ducting tube with a round cross-section is connected to the sampling tube, said cross-section being dimensioned so that it is sufficiently narrow to produce a maximum number of at least one of particle-particle and particle-wall impacts, with a transition tube being connected to this in which the cross-section continuously changes in size while changing from a round to a rectangular shape, and a jet ducting tube with a rectangular cross-section is connected to this and which extends to just in front of the measuring zone.

34. Apparatus for determining at least one of particle sizes and particle size distributions containing a device for sampling disperse material flows for performing a process for sampling disperse material flows in which an analysis substream is removed from a process mainstream for subsequent analysis, wherein the analysis substream is taken from the process mainstream via an extraction area which is smaller than the process mainstream cross-section and is defined independently of the same, and the extraction area follows an orbital curve across the process mainstream cross-section during extraction of the analysis substream, said apparatus being arranged within the process mainstream and a traversible sampling tube aligned in the direction opposite to the direction of the disperse material flow, wherein the sampling device, a sample transport system, a dispersing system, a measuring zone and a sample return stage are arranged within a pipe in the order recited, and the dispersion section can be briefly isolated by slewing the same in front of the outlet aperture of a jet pump to enable a reverse flow to be generated within the sampling tube in order to remove blockages.

35. Apparatus according to claim 34, structured and arranged for laser diffraction.

36. Apparatus for determining at least one of particle sizes and particle size distributions containing a device for sampling disperse material flows for performing a process for sampling disperse material flows in which an analysis substream is removed from a process mainstream for subsequent analysis, wherein the analysis substream is taken from the process mainstream via an extraction area which is smaller than the process mainstream cross-section and is defined independently of the same, and the extraction area follows an orbital curve across the process mainstream cross-section during extraction of the analysis substream, said apparatus being arranged within the process mainstream and a traversible sampling tube aligned in the direction opposite to the direction of the disperse material flow, wherein the sampling device, a sample transport system, a dispersing system, a measuring zone and a sample return stage are arranged within a pipe in the order recited, and the return feed of the analysis substream is performed via a jacket tube immediately downstream of the measuring zone in the direction of the pipe axis.

37. Apparatus for determining at least one of particle sizes and particle size distributions containing a device for sampling disperse material flows for performing a process for sampling disperse material flows in which an analysis substream is removed from a process mainstream for subsequent analysis, wherein the analysis substream is taken from the process mainstream via an extraction area which is smaller than the process mainstream cross-section and is defined independently of the same, and the extraction area follows an orbital curve across the process mainstream cross-section during extraction of the analysis substream, said apparatus being arranged within the process mainstream and a traversible sampling tube aligned in the direction opposite to the direction of the disperse material flow, wherein the sampling device, a sample transport system, a dispersing system, a measuring zone and a sample return stage are arranged within a pipe in the order recited, and a jet pump is arranged downstream of the measuring zone, by means of which the velocity of the particles to be measured in the measuring zone is increased such that the particles are located at the center of the measuring zone and thus contribute to the suppression of contamination of the measuring windows.

* * * * *